United States Patent [19]

Yoneda et al.

[11] 4,230,869

[45] Oct. 28, 1980

[54] PROCESS FOR PREPARING 5-(4-HYDROXYPHENYL)HYDANTOIN

[75] Inventors: Koji Yoneda, Amagasaki; Takehisa Ohashi; Tomoaki Nagamachi, both of Kobe; Hirotaka Fukumitsu, Kakogawa; Satomi Takahashi, Kobe, all of Japan

[73] Assignee: Kanegafuchi Kagaku Kogyo Kabushiki Kaisha, Osaka, Japan

[21] Appl. No.: 887,132

[22] Filed: Mar. 16, 1978

[30] Foreign Application Priority Data

Mar. 18, 1977 [JP] Japan .................................. 52-30824
Feb. 25, 1978 [JP] Japan .................................. 53-21305

[51] Int. Cl.³ .......................................... C07D 233/78
[52] U.S. Cl. ..................................... 548/314; 260/444
[58] Field of Search ......................................... 548/314

[56] References Cited

U.S. PATENT DOCUMENTS 2,687,416  8/1954  Persch et al. ........................ 548/314
3,439,048  4/1969  Biller .................................... 568/804
3,860,631  1/1975  Gleason et al. ................... 260/471 C

OTHER PUBLICATIONS

Ben-Et et al., Chemical Communications, 1969, p. 376.
Morikawa et al., Chem. Abst., 1971, vol. 74, No. 100043n.
Ware, Chem. Revs., 1950, vol. 46, pp. 414–415.
Noller, Chemistry of Organic Compounds, Sanders, Philadelphia, 1965, p. 555.
Harries et al., Ber. 1900, pp. 3418–3420.

*Primary Examiner*—Alan L. Rotman
*Assistant Examiner*—Natalia Harkaway
*Attorney, Agent, or Firm*—Armstrong, Nikaido, Marmelstein & Kubovcik

[57] ABSTRACT

A process for preparing 5-(4-hydroxyphenyl)hydantoin by reacting glyoxylic acid, urea and phenol in an aqueous medium in the presence of an acid at an elevated temperature. The hydantoin of high purity can be readily prepared in good yields.

5 Claims, No Drawings

PROCESS FOR PREPARING 5-(4-HYDROXYPHENYL)HYDANTOIN

BACKGROUND OF THE INVENTION

The present invention relates to a novel process for preparing 5-(4-hydroxyphenyl)hydantoin, and more particularly to a process for easily preparing 5-(4-hydroxyphenyl)hydantoin of high purity in good yields by reacting glyoxylic acid, urea and phenol in the presence of an acid.

5-(4-Hydroxyphenyl)hydantoin is an important intermediate of D-4-hydroxyphenylglycine which is employed for preparing semi-synthetic penicillins and semi-synthetic cephalosporins.

D-4-hydroxyphenylglycine has been generally prepared by chemically subjecting DL-4-hydroxyphenylglycine to optical resolution. However, such a process has the disadvantage that DL-4-hydroxyphenylglycine must be converted to derivatives such as esterification and acylation products prior to subjecting to optical resolution, or that expensive resolving reagents are required, and also the complication of process steps is unavoidable for racemizing the residual useless L-form.

Yamada et al found that DL-5-(4-hydroxyphenyl)-hydantoin can be almost quantitatively converted into D-N-carbamoyl-(4-hydroxyphenyl)glycine by causing cells or treated cells of specific microorganisms at act on the hydantoin in an aqueous medium at pH 7 to 10, as disclosed in U.S. Patent Application Ser. No. 764,635 now U.S. Pat. No. 3,094,741. D-N-carbamoyl(4-hydroxyphenyl)glycine can be converted into D-4-hydroxyphenylglycine in high yields, for instance, by reacting it with an equimolar amount of nitrous acid in the presence of a strong acid. The preparation of D-4-hydroxyphenylglycine according to such a process has no disadvantage incidental to the above-mentioned chemical method of optical resolution, and is technically and economically advantageous. Thus, DL-5-(4-hydroxyphenyl)hydantoin is an important intermediate of D-4-hydroxyphenylglycine.

Hitherto, it is known that 5-(4-hydroxyphenyl)hydantoin is synthesized by the reaction of 4-hydroxybenzaldehyde, ammonium bicarbonate and sodium cyanide according to the Bucherer-Berg's method. However, this method requires the use of dangerous sodium cyanide, and further the obtained crude hydantoin may contain large quantities of by-products caused by the oxidative side reaction of the phenol nucleus under an alkaline condition or may be colored.

SUMMARY OF THE INVENTION

The present invention provides a novel process for preparing 5-(4-hydroxyphenyl)hydantoin by reacting glyoxylic acid, urea and phenol in the presence of an acid. According to the present invention, 5-(4-hydroxyphenyl)hydantoin of high purity can be easily prepared in good yields.

DETAILED DESCRIPTION

The process of the present invention can be illustrated as follows:

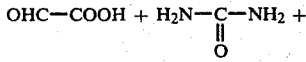

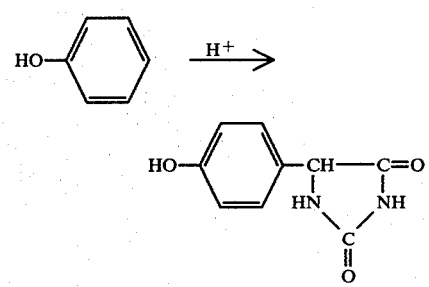

The main product of the above reaction is 5-(4-hydroxyphenyl)hydantoin, and the production of the isomer thereof, i.e. 5-(2-hydroxyphenyl)hydantoin is relatively small. Furthermore, since the latter is hard to crystallize, 5-(4-hydroxyphenyl)hydantoin can be easily obtained in a high state of purity by precipitating and separating it from the reaction mixture.

U.S. Pat. No. 3,860,631 discloses a process for preparing N-carbamoyl-2-(hydroxyphenyl)glycines by reacting glyoxylic acid, urea and phenol. According to the disclosure, glyoxylic acid, urea and phenol are reacted at room temperature for a long period of time, in the presence or absence of a small quantity of an acidic catalyst, in an organic solvent or without using a solvent.

In contrast, in the present invention the reaction is carried out in the presence of a relatively large quantity of an acid in an aqueous medium, usually at a temperature of not less than 40° C., preferably 60° to 100° C. Also, the product of the present invention is 5-(4-hydroxyphenyl)hydantoin, but not N-carbamoyl-2-(hydroxyphenyl)glycines. Thus, the present invention is entirely different from the process of U.S. Pat. No. 3,860,631 in the reaction conditions, objects and effects.

In the process of the present invention, one mole of glyoxylic acid stoichiometrically reacts with one mole each of urea and phenol, as illustrated by the above equation. However, in practice it is desirable to employ urea and phenol in excess, since the reaction rate is thus accelerated. Usually, urea and phenol are employed in amounts of 2 to 3 moles and 1.5 to 3 moles, respectively, per mole of glyoxylic acid.

Glyoxylic acid is employed in the form of glyoxylic acid monohydrate or in the form of an aqueous solution of glyoxylic acid. Salts of glyoxylic acid such as ammonium glyoxylate or sodium glyoxylate may also be employed so far as the reaction system is maintained acidic.

The reaction is usually carried out in an aqueous medium. Water is the most practical, but aqueous mixed solvents such as a water-alcohol, water-acetic acid or water-formic acid mixed solvent may also be availably employed.

In the present invention, it is essential to carry out the reaction in the presence of an acid. As the acid, inorganic acids such as mineral acids and organic acids such as formic acid or p-toluenesulfonic acid are suitably employed. Strong mineral acids such as hydrochloric acid or sulfuric acid are preferred. As to the acid, hereinafter the invention is explained with reference to the strong mineral acid. It is desirable to employ the strong acid in an amount so that the concentration of the strong acid in the reaction system is not less than 2 N. When it is desired to increase the reaction rate, the concentration of 4 N to 10 N is preferred. There is no upper limit of the concentration, but in general the increase of the yield is not particularly observed, even if the concentration is maintained at more than 10 N.

The reaction is carried out at a temperature of not less than 40° C., particularly 60° to 100° C. When the reaction temperature is less than 60° C., the reaction rate is slow, and particularly the reaction at a temperature of less than 40° C. is not practical. Also, when the reaction temperature is more than 100° C., the use of a pressure reactor such as an autoclave is required and is troublesome.

The 5-(4-hydroxyphenyl)hydantoin is prepared in such a manner that glyoxylic acid, urea and phenol are admixed in an aqueous medium and reacted in the presence of an acid, and is prepared in higher yield when glyoxylic acid and urea are first reacted in an acidic aqueous medium and then phenol or phenol and an acid are added to the reaction mixture and the reaction is completed. Although the details of the reaction mechanism are not clear, it is considered that glyoxylic acid and urea first react and a produced active intermediate then reacts with phenol to produce 5-(4-hydroxyphenyl)hydantoin, and is also considered so in the case of simultaneously reacting the reactants. In the process of the present invention, the acid concentration at the time an active intermediate produced from glyoxylic acid and urea reacts with phenol is an important factor. Therefore, in the two-step reaction procedure where phenol is added in the course of the reaction, it is desirable for increasing the rate of production of the hydantoin from glyoxylic acid to maintain the concentration of the strong acid in the reaction system at from 4 N to 10 N after adding phenol. Although the acid is also effective for the first reaction between glyoxylic acid and urea, a high concentration as stated above is not required. Usually a part of a prescribed amount of the strong acid is added in reacting glyoxylic acid with urea and after adding phenol, the residual acid is added. Of course, the whole acid can be added at once at the beginning of the reaction.

The reaction time varies depending on the acid concentration and the reaction temperature. For instance, in case of conducting the reaction at 90° C., glyoxylic acid and urea are reacted in the presence of an acid at 90° C. for 30 minutes to one hour and after adding phenol and adjusting the concentration of the strong acid in the system to 5 N, the reaction is further conducted at 90° C. for 5 to 6 hours.

In case of the two-step reaction, the yield of the hydantoin from glyoxylic acid can be increased by the use of an excess amount of phenol and a relatively large amount of an acid. However, such a condition is a factor of increasing the by-production of the isomer 5-(2-hydroxyphenyl)hydantoin and the use of an excess amount of phenol and a relatively large amount of an acid is not desirable, also from viewpoint of the waste water treatment.

In order to raise the yield of 5-(4-hydroxyphenyl)hydantoin from glyoxylic acid without employing a large excess of phenol and a large amount of the strong acid, there is preferred a reaction manner where glyoxylic acid is gradually added to a reaction system containing urea, phenol and an acid.

There is seen a difference in effect between the reaction manner of gradually adding glyoxylic acid and the two-step reaction manner as follows: For instance, when the reaction is carried out under the conditions that approximately equimolar amounts of glyoxylic acid and phenol are employed, the strong acid concentration in the reaction system is about 3 N, the reaction temperature is at 93° C. and the reaction time is 20 hours, the yield of 5-(4-hydroxyphenyl)hydantoin by the method of gradually adding glyoxylic acid increases 5% to 10% by mole as compared with the yield by the two-step reaction. Also, in case of the method of gradually adding glyoxylic acid the ratio of the produced 5-(4-hydroxyphenyl)hydantoin to the by-produced isomer 5-(2-hydroxyphenyl)hydantoin is from 5.5 to 5.7, whereas in case of the two-step reaction the ratio is from 4.1 to 4.3. Further, when the reaction is carried out at 65° C. according to the above procedures, the yield of 5-(4-hydroxyphenyl)hydantoin by the method of gradually adding glyoxylic acid increases 10% to 15% by mole as compared with the yield by the two-step reaction. Also, the ratio of 5-(4-hydroxyphenyl)hydantoin to the isomer is from 6.9 to 7.2 and increases as compared with the ratio of 4.8 to 5.0 in the two-step reaction. Thus, the reaction manner of gradually adding glyxoylic acid has the advantage that the rate of production of the hydantoin rises and moreover the amount of the by-produced 5-(2-hydroxyphenyl)hydantoin decreases and consequently 5-(4-hydroxyphenyl)hydantoin can be isolated and obtained in an increased yield.

Glyoxylic acid is added dropwise to a mixture containing urea, phenol and an acid at a prescribed temperature, usually over 3 to 20 hours. When the addition of glyoxylic acid is completed in a relatively short time, for instance, in 2 hours, the yield of 5-(4-hydroxyphenyl)hydantoin does not increase.

In case of conducting the reaction in such a manner as gradually adding glyoxylic acid, a large amount of the strong acid is not required, but when the concentration of the strong acid in the reaction system is less than 2 N, the reaction is slow and, therefore, the concentration is maintained not less than 2 N. Also, 2 to 2.5 moles of urea and 1 to 1.5 moles of phenol are preferably employed, respectively, per mole of glyoxylic acid.

The reaction time varies depending on the strong acid concentration and the reaction temperature. For instance, an aqueous solution of glyoxylic acid is gradually added to an aqueous solution of urea, phenol and an acid over 3 to 20 hours, while maintaining the solution containing urea, phenol and acid at a temperature of 60° to 100° C., and after adding glyoxylic acid the reaction is further continued at a temperature of 60° to 100° C. with agitation and is completed in 6 to 25 hours from the beginning of the addition of glyoxylic acid.

In the process of the present invention, the 5-(4-hydroxyphenyl)hydantoin produced by reacting glyoxylic acid, urea and phenol in the presence of an acid can be readily isolated from the reaction mixture by after distilling away the unreacted phenol and cooling to precipitate the hydantoin, or after adding water to the reaction mixture to precipitate the hydantoin, or after neutralizing the acid with an aqueous alkali solution and cooling to ordinary temperature to precipitate the hydantoin, filtering the precipitated hydantoin. In the reaction according to the present invention, the para-position of the phenol nucleus reacts in preference to the ortho-position, and the by-produced 5-(2-hydroxyphenyl)hydantoin is less than 5-(4-hydroxphenyl)hydantoin. Moreover, the by-product is hard to crystallize and, therefore, nearly pure DL-5-(4-hydroxyphenyl)hydantoin can be obtained by merely washing the obtained precipitate with water. The thus obtained hydantoin can be employed as it is in the next step of converting into D-N-carbamoyl-(4-hydroxyphenyl)glycine. As occasion demands, the obtained hydantoin may be, of course, purified in such a manner as recrystallization.

As stated above, 5-(4-hydroxyphenyl)hydantoin of high purity can be readily prepared in good yields by reacting glyoxylic acid, urea and phenol in the presence of an acid according to the process of the present invention, and thus the present invention provides a process for the preparation of 5-(4-hydroxyphenyl)hydantoin which is extremely available for the preparation of D-4-hydroxyphenylglycine.

The present invention is more partricularly described and explained by means of the following Examples, in which all % are % by weight unless otherwise stated. These Examples are intended to illustrate the invention and are not to be construed to limit the scope of the invention.

Also, the term "yield" as used in Examples means mole % yield of 5-(4-hydroxyphenyl)hydantoin to the employed glyoxylic acid.

EXAMPLE 1

A mixture of 0.92 g. (10 millimoles) of glyoxylic acid monohydrate, 1.80 g. (30 millimoles) of urea, 5.0 ml. of water and 0.30 ml. of a 36% hydrochloric acid was stirred at 90° C. for 60 minutes, and after further adding 2.82 g. (30 millimoles) of phenol, 3.0 ml. of water and 12.0 ml. of a 36% hydrochloric acid to the mixture, the reaction was further carried out at 90° C. for 6 hours with stirring. The reaction mixture was concentrated to one-half of its original volume under reduced pressure to remove the unreacted phenol, and after adding 20 ml. of water, the reaction mixture was allowed to stand. The resulting white precipitate was filtered and washed with water, and then dried to give 1.18 g. of 5-(4-hydroxyphenyl)hydantoin. The purity was over 98% and the yield was 61.5% by mole.

The thus obtained precipitate was recrystallized from water to give 1.06 g. of the purified 5-(4-hydroxyphenyl)hydantoin. The melting point was 263° to 265° C. (decomposition) and was in good agreement with the literature value [J. Amer. Chem. Soc., Vol. 47, 191(1925)]. The infrared absorption spectrum and the ultraviolet absorption spectrum agreed with those of 5-(4-hydroxyphenyl)hydantoin prepared from 4-hydroxybenzaldehyde, ammonium bicarbonate and sodium cyanide by a known method.

EXAMPLE 2

A mixture of 0.92 g. (10 millimoles) of glyoxylic acid monohydrate, 1.80 g. (30 millimoles) of urea, 5.0 ml. of water and 5.0 ml. of a 36% hydrochloric acid was stirred at 90° C. for 30 minutes, and after adding 2.82 g. (30 millimoles) of phenol and additional water and a 36% hydrochloric acid in amounts shown in Table 1, the reaction was further carried out at 90° C. for 6 hours with stirring. After the completion of the reaction, the reaction mixture was treated in the same manner as in Example 1.

The amounts and yields of the obtained 5-(4-hydroxyphenyl)hydantoin are shown in Table 1.

TABLE 1

| Run No. | Additional 36 % HCl ml. | Additional Water ml. | 5-(4-Hydroxyphenyl)hydantoin Amount g. | Yield % by mole |
|---|---|---|---|---|
| 1 | 0 | 10.0 | 0.80 | 41.7 |
| 2 | 1.0 | 9.0 | 0.95 | 49.5 |
| 3 | 3.0 | 7.0 | 1.10 | 57.3 |
| 4 | 5.0 | 5.0 | 1.09 | 56.8 |
| 5 | 15.0 | 0 | 1.06 | 55.2 |

EXAMPLE 3

A mixture of 0.92 g. (10 millimoles) of glyoxylic acid monohydrate, 1.80 g. (30 millimoles) of urea, 10.0 ml. of water and 10.0 ml. of a 36% hydrochliric acid was heated for 30 minutes with stirring. After adding 2.82 g. (30 millimoles) of phenol, the reaction was further carried out under the temperature and time conditions shown in Table 2. After the completion of the reaction, the reaction mixture was treated in the same manner as in Example 1.

The amounts and yields of the obtained 5-(4-hydroxyphenyl)hydantoin are shown in Table 2.

TABLE 2

| Run No. | Reaction temperature °C. | Reaction time* hour | 5-(4-Hydroxyphenyl)hydantoin Amount g. | Yield % by mole |
|---|---|---|---|---|
| 1 | 45 | 6 | 0.91 | 47.4 |
| 2 | 45 | 8 | 1.00 | 52.1 |
| 3 | 60 | 6 | 1.12 | 58.5 |
| 4 | 60 | 8 | 1.16 | 60.2 |
| 5 | 90 | 6 | 1.12 | 58.4 |

*Reaction time shows the time from the addition of phenol.

EXAMPLE 4

A mixture of 0.92 g. (10 millimoles) of glyoxylic acid monohydrate, 1.20 g. (20 millimoles) of urea, 5.0 ml. of water and 5.0 ml. of a 36% hydrochloric acid was stirred at 90° C. for 30 minutes, and after adding 0.94 g. (10 millimoles) of phenol, 9.0 ml. of water and 1.0 ml. of a 36% hydrochloric acid, the reaction was further carried out at 90° C. for 6 hours with stirring. After the completion of the reaction, the reaction mixture was treated in the same manner as in Example 1 to give 0.91 g. of 5-(4-hydroxyphenyl)hydantoin. The purity was over 98% and the yield was 47.4% by mole.

EXAMPLE 5

A mixture of 2.30 g. (25 millimoles) of glyoxylic acid monohydrate, 3.75 g. (62.5 millimoles) of urea and 10.7 g. of a 52% sulfuric acid was stirred at 90° C. for 30 minutes and after adding 4.70 g. (50 millimoles) of phenol, the reaction was further carried out at 90° C. for 6 hours with stirring. After the completion of the reaction, the reaction mixture was treated in the same manner as in Example 1 to give 2.86 g. of 5-(4-hydroxyphenyl)hydantoin. The purity was over 98% and the yield was 59.5% by mole.

EXAMPLE 6

A mixture of 0.92 g. (10 millimoles) of glyoxylic acid monohydrate, 1.80 g. (30 millimoles) of urea, 2.82 g. (30 millimoles) of phenol, 10.0 ml. of water and 10.0 ml. of a 36% hydrochloric acid was stirred at 90° C. for 6 hours. After the completion of the reaction, the reaction mixture was treated in the same manner as in Example 1 to give 0.76 g. of 5-(4-hydroxyphenyl)hydantoin. The yield was 39.5% by mole.

EXAMPLE 7

A mixture of 0.92 g. (10 millimoles) of glyoxylic acid monohydrate, 1.80 g. (30 millimoles) of urea, 2.82 g. (30 millimoles) of phenol, 5.0 ml. of water and 0.30 ml. of a 36% hydrochloric acid was stirred at 90° C. for one hour. To the mixture were then added 5.0 ml. of water and 10.0 ml. of a 36% hydrochloric acid, and the reaction was further carried out at 90° C. for 6 hours with stirring. After the completion of the reaction, the reaction mixture was treated in the same manner as in Example 1 to give 0.95 g. of 5-(4-hydroxyphenyl)hydantoin. The yield was 49.4% by mole.

EXAMPLE 8

To a mixture of 48.0 g. (800 millimoles) of urea, 44.0 g. of a 90% aqueous solution of phenol (424 millimoles of phenol), 124.0 g. of a 36% hydrochloric acid and 168.0 ml. of water was added dropwise 72.2 g. of a 41% aqueous solution of glyoxylic acid (400 millimoles of glyoxylic acid) over 6 hours at 65° C. with stirring. After the addition, the reaction was further continued at 65° C. for 15 hours with stirring. After the completion of the reaction, the reaction mixture was adjusted to pH 7 with a 10% aqueous solution of sodium hydroxide, and 5-(4-hydroxyphenyl)hydantoin was precipitated at 35° C. with stirring. The precipitate was filtered, washed with water and dried to give 44.5 g. of 5-(4-hydroxyphenyl)hydantoin. The purity was over 98% and the yield was 57.9% by mole.

EXAMPLE 9

To a mixture of 6.0 g. (100 millimoles) of urea, 5.5 g. of a 90% aqueous solution of phenol (53 millimoles of phenol), 15.5 g. of a 36% hydrochloric acid and 21.0 ml. of water was added 9.0 g. of a 41% aqueous solution of glyoxylic acid (50 millimoles of glyoxylic acid) at 93° C. with stirring with taking the time shown in Table 3. The reaction was further continued and completed in 20 hours from the beginning of the addition of glyoxylic acid. The reaction mixture was analyzed by a liquid chromatography to determine the yield of 5-(4-hydroxyphenyl)hydantoin and the ratio of 5-(4-hydroxyphenyl)hydantoin to the isomeric 5-(2-hydroxyphenyl)hydantoin.

The results are shown in Table 3.

As a comparison, the two-step reaction was also carried out as follows: A mixture of glyoxylic acid, urea and hydrochloric acid was stirred at 93° C. for 30 minutes and after adding phenol, the reaction was further carried out at 93° C. for 19.5 hours. The results are also shown in Table 3, Run No. 5.

TABLE 3

| Run No. | Time required for adding glyoxylic acid minute | Yield of 5-(4-hydroxyphenyl)-hydantoin % by mole | Ratio of isomers |
|---|---|---|---|
| 1 | 140 | 60.4 | 5.5 |
| 2 | 240 | 63.1 | 5.7 |
| 3 | 360 | 66.0 | 5.6 |
| 4 | 600 | 66.5 | 5.7 |
| 5 | — | 55.5 | 4.3 |

EXAMPLE 10

The procedures of Example 9 were repeated except that the reaction was carried out at 65° C. and the time for adding glyoxylic acid was changed as shown in Table 4. The reaction mixture was worked up in the same manner as in Example 9.

The yields of 5-(4-hydroxyphenyl)hydantoin and the ratios of 5-(4-hydroxyphenyl)hydantoin to the isomeric 5-(2-hydroxyphenyl)hydantoin are shown in Table 4.

As a comparison, the two-step reaction was also carried out as follows: A mixture of glyoxylic acid, urea and hydrochloric acid was stirred at 65° C. for 40 minutes and after adding phenol, the reaction was further carried out at 65° C. for 19 hours and 20 minutes. The results are also shown in Table 4, Run No. 6.

TABLE 4

| Run No. | Time required for adding glyoxylic acid minute | Yield of 5-(4-hydroxyphenyl)-hydantoin % by mole | Ratio of isomers |
|---|---|---|---|
| 1 | 120 | 54.3 | 6.9 |
| 2 | 180 | 61.0 | 6.9 |
| 3 | 300 | 63.7 | 7.0 |
| 4 | 360 | 64.1 | 7.2 |
| 5 | 600 | 65.5 | 7.1 |
| 6 | — | 47.3 | 4.8 |

EXAMPLE 11

To a mixturr of 24.0 g. (400 millimoles) of urea, 22.0 g. of a 90% aqueous solution of phenol (212 millimoles of phenol), 62.0 g. of a 36% hydrochloric acid and 84.0 ml. of water was added dropwise 36.1 g. of a 41% aqueous solution of glyoxylic acid (200 millimoles of glyoxylic acid) over 4 hours at 95° C. with stirring. After the addition, the reaction was further continued at 95° C. for 16 hours with stirring. After the completion of the reaction, the reaction mixture was neutralized with a 10% aqueous solution of sodium hydroxide, and the produced 5-(4-hydroxyphenyl)hydantoin was precipitated at 40° C. with stirring. The precipitate was filtered, washed with water and dried to give 22.1 g. of 5-(4-hydroxyphenyl)hydantoin. The purity was over 98% and the yield was 57.6% by mole.

The same amounts of glyoxylic acid, urea, phenol, hydrochloric acid and water as the above were employed and the reaction was carried out in the following manner. To a mixture of glyoxylic acid, urea and hydrochloric acid was added phenol over 4 hours at 95° C. with stirring, and the reaction was further continued at 95° C. for 16 hours with stirring. The reaction mixture was then treated in the same manner as the above. In this case, the amount of the obtained 5-(4-hydroxyphenyl)hydantoin was 17.5 g. and the yield was 45.6% by mole.

EXAMPLE 12

To a mixture of 6.0 g. (100 millimoles) of urea, 7.8 g. of a 90% aqueous solution of phenol (75 millimoles of phenol), 15.5 g. of a 36% hydrochloric acid and 21.0 ml. of water was added dropwise 9.0 g. of a 41% aqueous solution of glyoxylic acid (50 millimoles of glyoxylic acid) over 12 hours at 64° C. with stirring. After the addition, the reaction was further continued at 65° C. for 14 hours with stirring. The reaction mixture was then analyzed by a liquid chromatography to determine the amounts and yields of hydantoins and the ratio of isomers.

The amount of the produced 5-(4-hydroxyphenyl)hydantoin was 6.1 g. (yield: 63.6% by mole), and the amount of the produced 5-(2-hydroxyphenyl)hydantoin was 1.0 g. (yield: 10.5% by mole). The ratio of 5-(4-hydroxyphenyl)hydantoin to 5-(2-hydroxyphenyl)hydantoin was 6.1.

EXAMPLE 13

To a mixture of 48.0 g. (800 millimoles) of urea, 44.0 g. of a 90% aqueous solution of phenol (424 millimoles of phenol), 55.0 g. of a 98% sulfuric acid and 274.0 ml. of water was added dropwise 72.2 g. of a 41% aqueous solution of glyoxylic acid (400 millimoles of glyoxylic acid) over 12 hours at 60° C. with stirring. After the addition, the reaction was further continued at 60° C. for 10 hours with stirring. The reaction mixture was adjusted to pH 7 with a 10% aqueous solution of sodium hydroxide, and 5-(4-hydroxyphenyl)hydantoin was precipitated at 35° C. with stirring. The precipitate was filtered, washed with water and dried to give 44.5 g. of 5-(4-hydroxyphenyl)hydantoin. The purity was over 98% and the yield was 57.9% by mole.

What we claim is:

1. A process for preparing 5-(4-hydroxyphenyl)hydantoin which comprises subjecting glyoxylic acid, urea and phenol to reaction in an aqueous medium at a temperature of not less than 40° C. in the presence of a strong mineral acid, the concentration of which in the reaction system is not less than 2 N.

2. The process of claim 1, wherein said reaction is carried out by reacting glyoxylic acid and urea, adding phenol to the resulting reaction mixture and subjecting the whole mixture to further reaction.

3. The process of claim 2, wherein urea and phenol are employed in amounts of 2 to 3 moles and 1.5 to 3 moles, respectively, per mole of glyoxylic acid.

4. The process of claim 1, wherein said reaction is carried out by gradually adding glyoxylic acid to a mixture containing urea, phenol and the strong mineral acid.

5. The process of claim 4, wherein urea and phenol are employed in amounts of 2 to 2.5 moles and 1 to 1.5 moles, respectively, per mole of glyoxylic acid.

* * * * *